US012606781B2

(12) United States Patent
Viiru et al.

(10) Patent No.: US 12,606,781 B2
(45) Date of Patent: Apr. 21, 2026

(54) BIOGAS REACTOR AND METHODS FOR PRODUCING BIOGAS

(71) Applicant: BGCNORDIC OY, Vaajakoski (FI)

(72) Inventors: Henri Viiru, Vaajakoski (FI); Pasi Kolehmainen, Kuohu (FI)

(73) Assignee: BGCNORDIC OY, Vaajakoski (FI)

( * ) Notice: Subject to any disclaimer, the term of this patent is extended or adjusted under 35 U.S.C. 154(b) by 920 days.

(21) Appl. No.: 17/774,283

(22) PCT Filed: Nov. 4, 2020

(86) PCT No.: PCT/FI2020/050727
§ 371 (c)(1),
(2) Date: May 4, 2022

(87) PCT Pub. No.: WO2021/089918
PCT Pub. Date: May 14, 2021

(65) Prior Publication Data
US 2022/0389358 A1     Dec. 8, 2022

(30) Foreign Application Priority Data

Nov. 4, 2019     (FI) ..................................... 20195946

(51) Int. Cl.
*C12M 1/107*          (2006.01)
*C12M 1/02*           (2006.01)
(Continued)

(52) U.S. Cl.
CPC ............ *C12M 21/04* (2013.01); *C12M 41/22* (2013.01); *C12M 23/06* (2013.01); *C12M 23/34* (2013.01); *C12M 23/44* (2013.01)

(58) Field of Classification Search
CPC ...... C12M 21/04; C12M 41/22; C12M 23/06; C12M 23/34; C12M 23/44; C12M 1/02;
(Continued)

(56) References Cited

U.S. PATENT DOCUMENTS

| | | | |
|---|---|---|---|
| 2009/0134173 A1* | 5/2009 | Liang ..................... | C12M 27/02 |
| | | | 220/563 |
| 2013/0089925 A1* | 4/2013 | Damren ................ | F28F 9/0131 |
| | | | 435/303.1 |
| 2019/0316073 A1 | 10/2019 | Chuo et al. | |

FOREIGN PATENT DOCUMENTS

| | | |
|---|---|---|
| CN | 103881901 A | 6/2014 |
| CN | 103016858 B | 7/2015 |
| (Continued) | | |

OTHER PUBLICATIONS

Machine Translation of EP-0374708 A1 (Year: 2025).*
(Continued)

*Primary Examiner* — Michael L Hobbs
(74) *Attorney, Agent, or Firm* — FisherBroyles, LLP

(57) ABSTRACT

A biogas reactor is disclosed in which biogas is formed from organic matter. The biogas reactor includes a wall to form a tank structure enclosing a tubular reactor space in which organic matter can be placed to form biogas. The wall forming the tank structure is comprised of a helically wound hollow pipe profile to form a spiral arrangement. The hollow space within the hollow pipe profile accommodates a heat-transfer medium to influence the temperature of organic matter in the reactor space. Connections are provided for feeding organic matter to the reactor space and removing it from the reactor space, and one or more connections are provided for removing biogas from the reactor space. The invention also concerns methods for producing biogas and for manufacturing a biogas reactor.

20 Claims, 9 Drawing Sheets

(51) Int. Cl.

| | | |
|---|---|---|
| *C12M 1/12* | (2006.01) | |
| *C12M 1/00* | (2006.01) | |
| *C12M 3/00* | (2006.01) | |

(58) Field of Classification Search
CPC ....... C12M 1/107; C12M 1/113; Y02E 50/30;
B01J 7/02; C02F 11/04; F16L 9/18; F28D
7/04
See application file for complete search history.

(56) References Cited

FOREIGN PATENT DOCUMENTS

| | | | | | |
|---|---|---|---|---|---|
| EP | 0374708 | A1 | * | 6/1990 | ............ C12M 45/02 |
| FI | 128098 | B | | 9/2019 | |
| FR | 3012346 | A1 | | 5/2015 | |
| GB | 673075 | A | | 6/1952 | |
| KR | 100780674 | B1 | | 11/2007 | |
| WO | 9519424 | A1 | | 7/1995 | |

OTHER PUBLICATIONS

International Search Report in corresponding International Application No. PCT/FI2020/050727, mailed Feb. 17, 2021, 2 pages.
Finnish Search Report in corresponding Finnish Patent Application No. 20195946, dated May 27, 2020, 3 pages, English translation.
Written Opinion of the International Searching Authority in corresponding International Application No. PCT/FI2020/050727, dated Jan. 2015, 7 pages.

* cited by examiner

BIOGAS REACTOR AND METHODS FOR PRODUCING BIOGAS

CROSS-REFERENCE TO RELATED APPLICATIONS

This application is a U.S. National Stage of International Patent Application No: PCT/FI2020/050727 filed on Nov. 4, 2020, which claims benefit of Finland Patent Application No. FI 20195946 filed on Nov. 4, 2019.

FIELD OF THE INVENTION

The invention concerns a biogas reactor. In addition, the invention also concerns methods for producing biogas.

BACKGROUND OF THE INVENTION

Biogas is a gas arising in anaerobic conditions, the microbes of which are formed from organic matter. Biogas contains a great deal of methane, some carbon dioxide, and a small amount of sulphuric compounds.

The biogas process can be run at a psychrophilic (0-15° C.), mesophilic (15-45° C.), or thermophilic (50-75° C.) temperature. These all have different bacterial strains. The process is the more vigorous the higher its temperature. The usual temperature is mesophylic. Using it obtains good gas production and easy controllability. The gas is a renewable biofuel, which is most usually used to produce electricity and heat. In its properties, biogas is comparable to natural gas.

Biogas can be produced using biogas reactors, for which many different technical solutions have been developed. Reactors can be roughly divided into two basic types. These are complete-mix and plug-flow reactors. Complete-mix reactors can, for example, operate and mix continuously. Material is then pumped into the reactor and the same amount is also removed from it, the amount of mass thus remaining constant. It has the advantages of automation of the feeds and a relatively constant gas production.

A plug-flow reactor is a type particularly suitable for dry materials. In it organic matter is arranged in a horizontally arranged elongated reactor space. The mass to be processed in the reactor space travels, in the order it is fed, as a plug flow through the process, at the same time forming gas. This achieves a nearly constant delay time for the mass. The plug flow is created in a tubular reactor. The mass is fed into one end of the reactor and discharged at the other end. New mass cannot mix with the old, so bacterial liquid collected from the process can be fed into the mass to accelerate and/or stabilize the process. Gas is removed, for example, from the reactor's upper part. The reactor space forms a jacket with the cross-sectional profile of, for example, a rotational piece. This is arranged to the reactor's frame structures, which are generally of metal.

Yet another reactor type is a batch reactor. This is filled and emptied at regular intervals. Its advantage is ease of handling during the process and its drawback a relatively slow start to gas production and it is also laborious to empty.

In Finland, biogas is often produced in large biogas plants at landfill sites and farms. The raw material is usually organic waste. Examples of this are waste from the foodstuffs industry, domestic biowaste, or manure. In developing countries, instead of that, reactors are typically small underground tanks measuring a few cubic metres.

In biogas reactors, temperature control plays an essential part in the operability and control of the process. Taking the aforementioned into account, it is problematic to arrange heat-exchange means in connection with the reactor. Using the heat-exchange means, it should be possible to influence the process's temperature as precisely and effectively as possible, but nevertheless so that the structural solution remains simple, both to make and also to operate. In addition, the structural solution should be, for example, for logistical reasons, a light structure.

SUMMARY OF THE INVENTION

An object of the present invention is to create a biogas reactor, which, thanks to its construction, can be precisely controlled and regulated. Another object of the invention is to create methods for producing biogas and for manufacturing a biogas reactor, owing to which biogas can be produced with light and economical structural implementations and additionally using improved logistics concerning, for example, the arrangement of a biogas reactor at a biogas production site.

The above and other objects of the invention are achieved by providing, in one aspect of the invention, a biogas reactor comprising: a tank structure comprising a hollow pipe profile helically wound in a spiral arrangement to form a wall having a double-layer structure enclosing a tubular reactor space arranged inside the tank structure in which an organic matter can be placed to form biogas, wherein a spiral hollow space exists within the double-layer structure of the wall to accommodate a heat-transfer medium to influence a temperature of the organic matter placed in the tubular reactor space; connections to feed organic matter to the tubular reactor space and to remove organic matter from the tubular reactor space; and at least one connection to remove biogas from the tubular reactor space.

In the biogas reactor according to the invention, the tank structure is comprised of a hollow pipe profile wound in a spiral arrangement by helically winding the hollow pipe profile to form a double-layered structure of the wall forming the tank structure. In addition, the double-layered structure formed of the wall includes a hollow space for a heat-transfer medium. The tank structure is arranged to be formed from the pipe formed of the hollow pipe profile, for example, using a welding method in connection with its helical winding. Owing to the tank structure, the technical controllability of the reactor's process is improved.

One important advantage of the spiral structure is that due to the double-layered structure forming the wall of the tank structure, a clearly defined flow channel is formed. The heat-exchange medium circulating in the flow channel is thus forced, owing to the invention, to travel through the entire double-layered structure, i.e., the wall of the tank structure, and even more particularly through the heat-exchange structure formed by the spirally arranged pipe profile. The heat-transfer medium cannot then, for example, stratify anywhere in the double-layered structure, more generally in the wall of the tank structure. Instead, it is forced to circulate in a controlled manner in terms of flow, defined in an ordered manner, through the entire double-layered structure forming the tank structure and, in that way, to affect the tank structure throughout on every side of its large heat-exchange surface area, wherein according to the invention, the tank structure's wall is formed, for example, using rectangular pipe profile.

Another important advantage is that, owing to the invention, the feed and/or the flow direction relative to the reactor space and the organic matter to be placed in it and to the progress of the process are well taken into account owing to the invention. In other words, owing to the invention it becomes possible to target and control the temperature effect on the correct point in terms of the reactor and thus the process stage. The temperature effect can then be said to be location dependent in the case of the reactor structure and thus also of the process stage. The feed of the heat-transfer medium to a specific location of the tank structure affects, starting from that point, a specific direction defined by the flow channel formed by the profile pipe in the reactor structure. This is an essential advantage in terms of the process regulation and its controllability. It makes the process control precise.

The biogas reactor according to the invention, and especially its tank structure, can be mainly of a plastic material. Thus, its material can be recycled and can recycle. It is also light, durable, and is cheap to manufacture. It is corrosion-free, i.e., it neither rusts nor corrodes as a result of chemical reaction. The reactor's characteristic slippery surface also prevents deposits from adhering to the reactor's surface. The reactor also has a very long service life.

In addition, being light the reactor is easy to transport to its operating site and is also rapid and easy to install. The light and rigid structure permits the reactor to be made ready in production facilities and also if necessary to be moved afterwards to another operating site.

The biogas reactor's scalability also improves owing to the invention. The invention allows the achievement of cost-effectiveness in both the biogas reactor's manufacture and its operating costs (for example, own operation). Using a biogas reactor and method according to the invention, profitable gas production is achieved relative to investment costs. Other characteristic features of the invention are stated in the accompanying claims and additional achievable advantages are itemized in the description portion.

BRIEF DESCRIPTION OF THE DRAWINGS

In the following, the invention, which is not restricted to the embodiments described it, is described in detail with reference to the accompanying figures, in which.

DETAILED DESCRIPTION OF THE INVENTION

Figure 1:
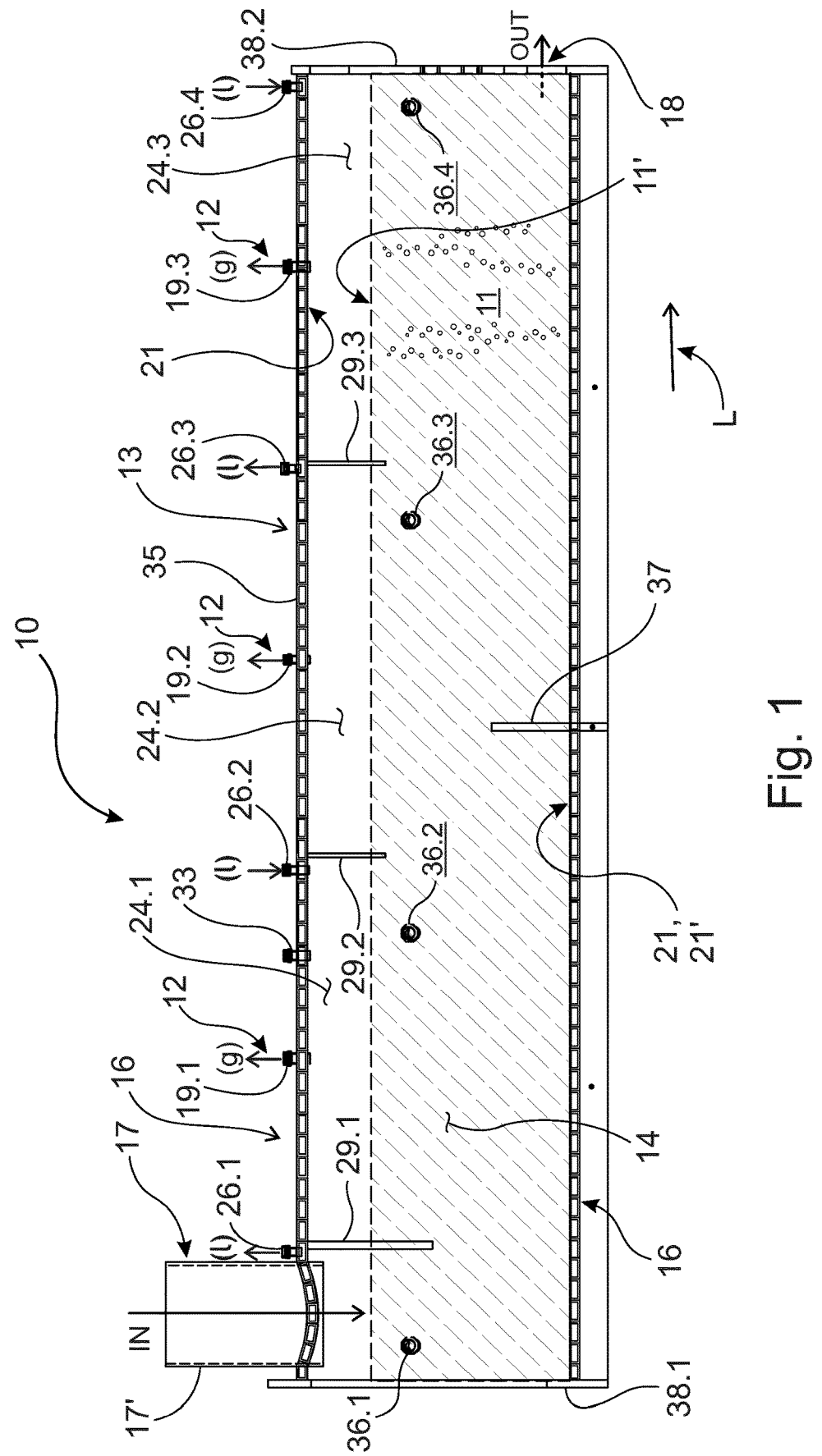
FIG. 1 shows a schematic diagram of one example of the biogas reactor seen in cross-section from the side.

FIG. 1 shows a schematic diagram of one example of the biogas reactor 10, seen from the side and in cross-section.

Figure 2:
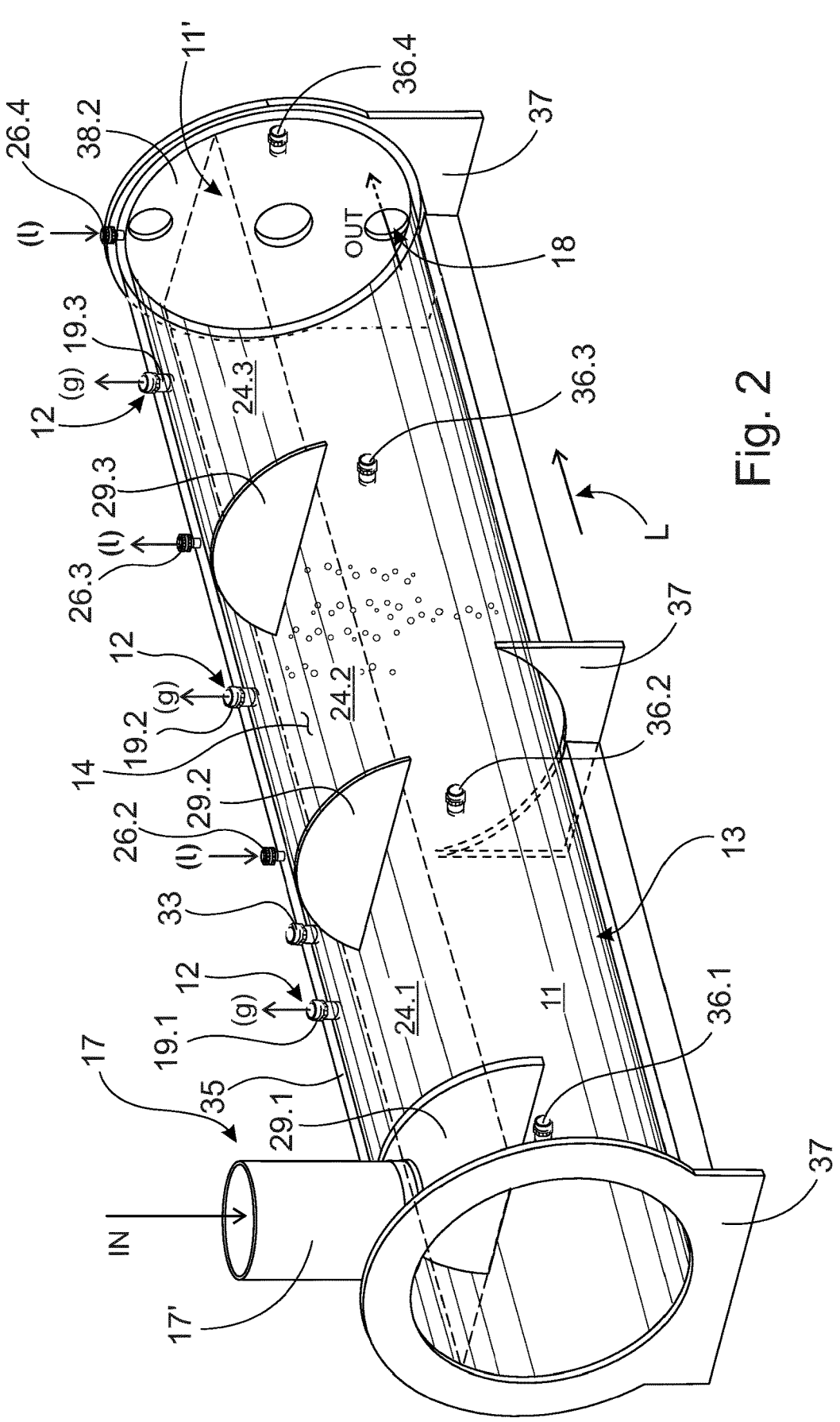
FIG. 2 shows an angled side view of the biogas reactor shown in FIG. 1.

For its part, FIG. 2 shows an angled side view of the biogas reactor 10 of FIG. 1, with the tank structure 13 transparent. The biogas reactor 10 is intended to form biogas 12, more generally gas, from organic matter 11. The organic matter 11 can also be called biomass. Examples of this are all kinds of organic waste, such as, for example, manure, waste water, and industrial reject fractions. Of course, the organic matter 11 need not necessarily be waste at all, but can be, for example, grown specifically for gas production.

To form biogas 12, the biogas reactor 10 includes a reactor space 14, in which the organic matter 11 can be placed to form biogas 12. The reactor space 14 is arranged to form a tank structure 13. The reactor space 14 is now a horizontally elongated, i.e., tubularly formed, cylindrical space. The cylindrical space is now defined by a wall 35 arranged to form the tank structure 13. The organic matter 11 is fed to the reactor space 14 as feed (IN) and correspondingly also removed from it (OUT). Thus, the organic matter 11 also progresses in the reactor space 14 at the same time as biogas 12 is formed from it, for example, in as such known processes. The biogas reactor 10 thus also includes connections 17, 18 for feeding the organic matter 11 into the reactor space 14 and for removing the organic matter 11 from the reactor space 14. The organic matters 11 can be fed from a feed connection 17', which can be in the vicinity of the reactor's 10 end 38.1. One or more of the connections, such as, for example, the outlet connection 18, can be implemented, for example, also in the form of a pump. The biogas reactor 10 can be, in its operating principle, for example, a plug-flow reactor. The feed/removal is sought to be implemented as the most even flow possible, so that the process conditions remain as even as possible.

Further, the biogas reactor 10, more particularly its tank structure 13, includes one or more connections 19.1-19.3 to take the biogas 12 formed in the reactor space 14 out from the reactor space 14 and thus from the biogas reactor 10. The biogas 12 arising as a result of, for example, the anaerobic decomposition of the organic matter 11, is collected through the connections 19.1-19.3. Biogas 12 recovery means (not shown) are attached to the connections 19.1-19.3.

The anaerobic decomposition can also be termed the digestion of the organic matter 11. This is the decomposition of the organic matter taking place in anaerobic conditions. Anaerobic micro-organisms are responsible for the digestion. The products arising from the digestion are mainly solids corresponding to humus, water, carbon dioxide, and methane gas that can be utilized, for example, in energy production. The methane content of the biogas arising in the digestion process is, for example, 50-70%. In digestion, nitrogen compounds reduce to ammonia and sulphur compounds to hydrogen sulphide. The digestion process can comprise four as such known main stages: hydrolyzation, acid fermentation, acetogenesis, and methanogenesis.

The biogas reactor 10 also includes heat-regulation means 16 for influencing the temperature of the reactor space 14 and even more particularly of the organic matter 11 to be placed in the reactor space 14. One can also speak of the reactor space 14 being arranged to be temperature regulated, i.e., of the reactor heating. The heat-regulation means 16 are arranged, in terms of heat exchange, in connection with the reactor space 14 in such a way that they can be used to either heat the material in the reactor space 14 and/or cool it. Thus, a change of state aimed at the heat-regulation means 16 also affects the reactor space 14 and the organic matter 11 placed in it, either heating or cooling it. Generally, heating or cooling, more generally the heat-regulation means 16 are intended to maintain the reactor space's 14, and thus also the organic matter's 11 temperature within the specific optimal limits for gas formation. Thus, affecting the temperature during the digestion process itself can be understood as maintaining the temperature.

Figure 3:
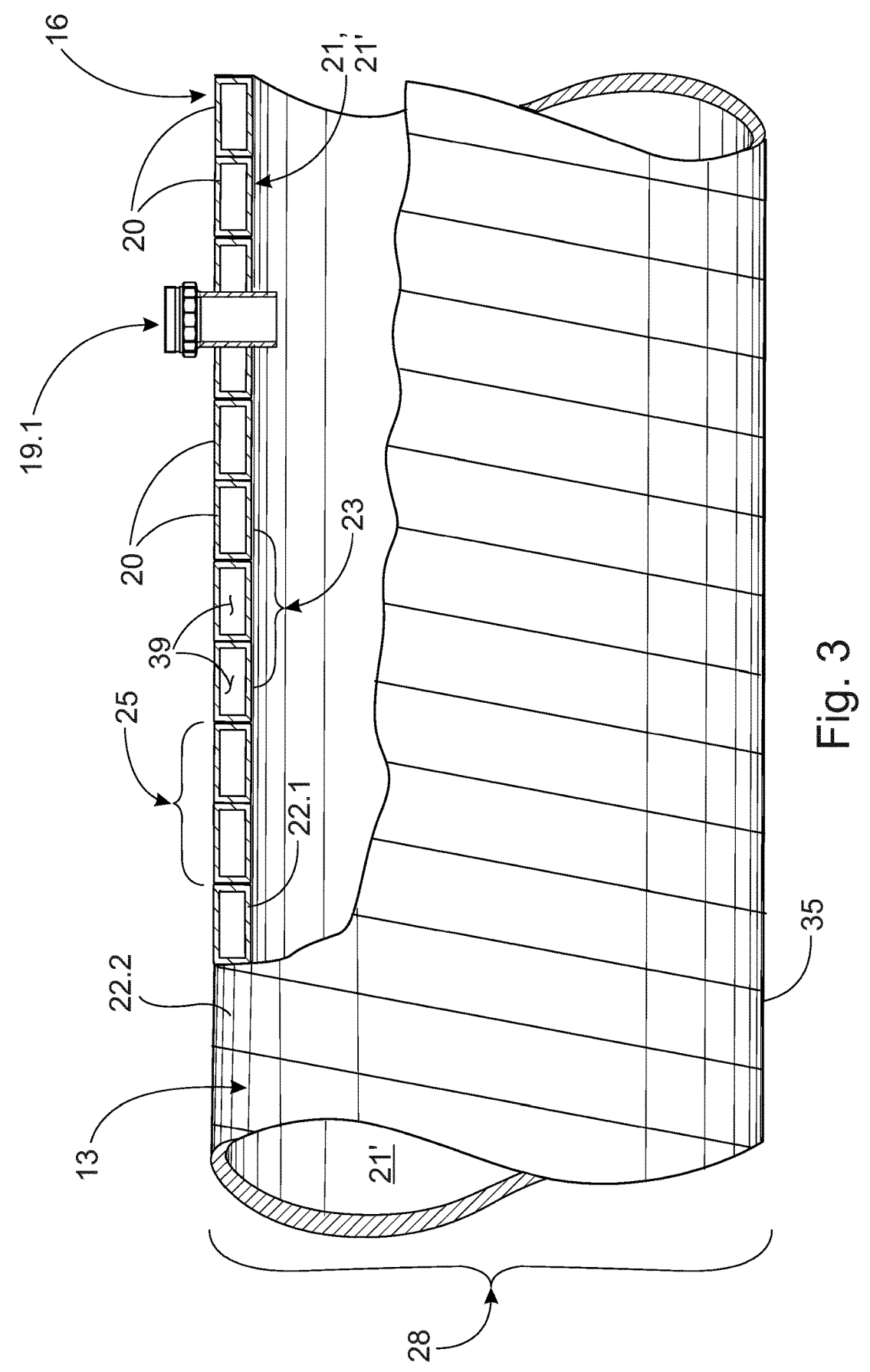
FIG. 3 shows a simplified schematic diagram of the biogas reactor's tank structure, seen in partial cross-section from the side.

By the heat-regulation means 16, more generally the reactor heating, is arranged to be formed, of the tank structure 13 of the biogas reactor 10 a double-layer structure of the wall 35 of the tank structure 13 seen in FIG. 1 and particularly in FIG. 3, for forming the hollow space 39 for the heat-transfer medium 27. The double-layer structure of the wall 35 of the tank structure 13 formed as the heat-regulation means 16 can then form most of the tank structure's 13 load-bearing structure. In other words, the heat-regulation means 16 are then integrated, i.e., built into the tank structure 13 of the biogas reactor 10 i.e., into its wall 35. Thus, the biogas reactor's 10 reactor space 14, and equally also the outside of the tank structure 13, can be free of the heat-regulation means 16. In the reactor space 14 the heat-regulation means 16 would dirty and outside the tank structure 13 they would hinder, for example, the possible insulation of the biogas reactor 10. Integrating the heat-regulation means 16 in the tank structure's 13 wall 35, and especially inside the wall 35, simplifies the biogas reactor's 10 construction.

The heat-regulation means 16 belonging to the tank structure 13 are arranged to form an essential part of the biogas reactor's 10 frame to stiffen it and thus also to make it self-supporting. The biogas reactor 10 will then not necessarily need at all, around the tank structure 13 that defines and delimits the reactor space 14, a frame structure stiffening the biogas reactor 10. Instead, this property is created using the tank-structure solution formed by the heat regulation means 16. The heat-regulation means 16 integrated in the tank structure 13, i.e., the wall 35 itself, carry most of the load. Owing to the invention the biogas reactor's 10 tank structure 13 and more particularly the tank structure's 13 wall 35 itself acts as a heat exchanger. Using its double-layer structure the tank structure's 13 wall 35 provides even and well-controlled reactor 10 heating. The biogas reactor 10 is then process-technically precisely controllable and regulatable (heating/reactor's loading). This is important, as even small swings in the reactor space's 14 temperature can cause in a known manner an unfavourable effect of gas formation. Thanks to the construction, the temperature is more even. Cold/very hot points do not form in the reactor 10.

Figure 4:
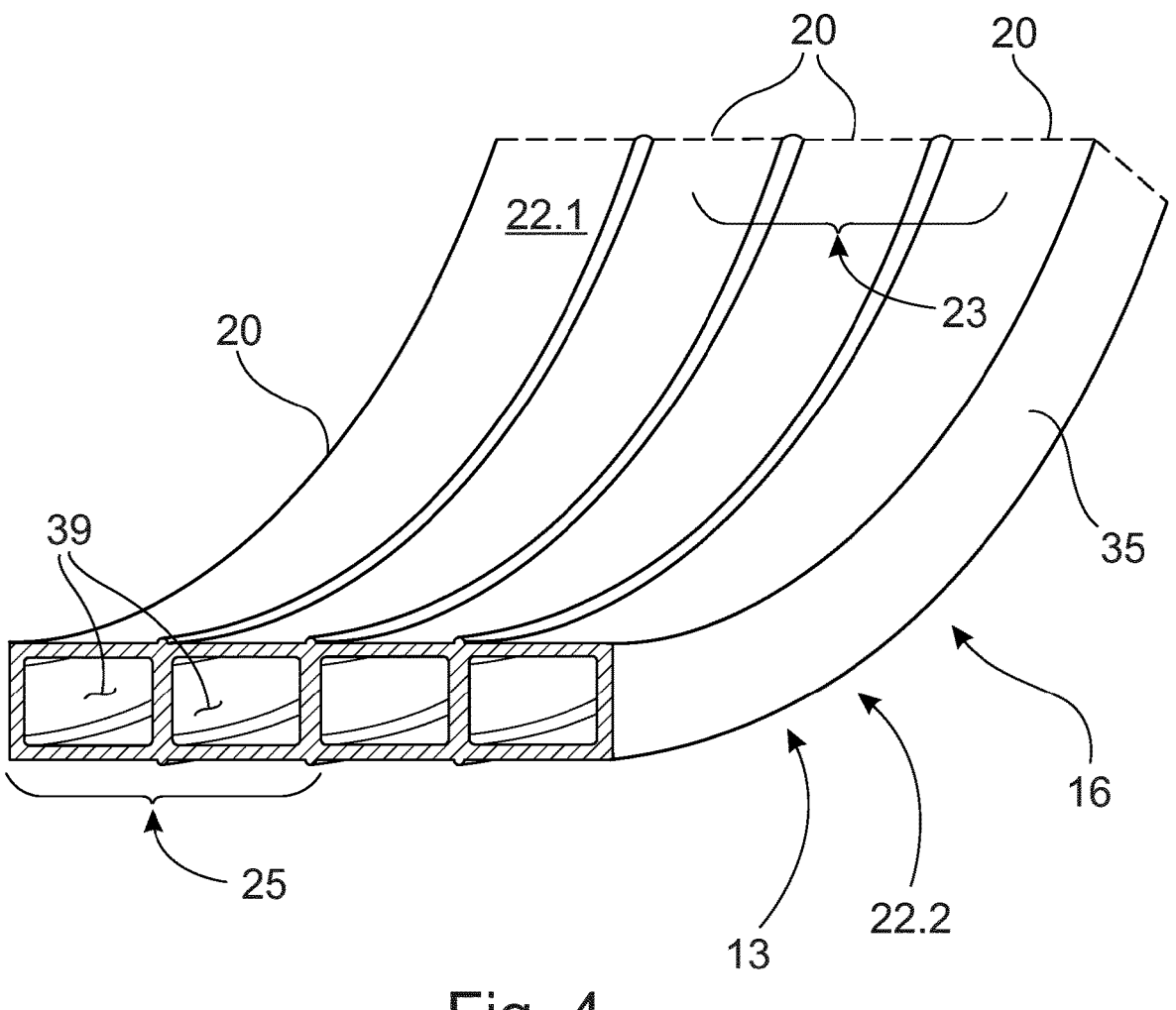
FIG. 4 shows an example of the tank structure's wall structure in partial cross-section.

FIGS. 3 and 4 show an example of the biogas reactor's 10 tank structure 13, in which heat-regulation means 16 are also integrated, according to the invention. The heat-regulation means 16 can also be said to form most of the tank's 13 load-bearing structure. The tank structure 13, particularly the wall 35, has a hollow jacket and thus also a double-layer structure. In other words, in the double-layer structure formed by the wall 35 of the tank structure 13, there is a hollow space 39 for the heat-transfer medium 27. For example, a liquid heat-transfer medium 27 is circulated in the hollow 39 formed inside the wall 35, to affect the temperate of the reactor space 14 and thus of the organic matter 11 to be placed in it.

Stated more generally, the biogas reactor's 10 heat-regulation means 16 are formed from the hollow pipe profile 20. This pipe profile 20 is arranged in a spiral arrangement by helically winding an elongated pipe 28 of pipe profile 20 to form from the pipe profile 20 the tank structure's 13 wall 35, inside which tank structure 13 is the tubular reactor space 14. Thus, the heat-regulation means 16 are not, for example, in the reactor space 14, where they could dirty. Thus, the reactor space 14 is unobstructed in the case of the heat-regulation means 16. Owing to the invention, the hollow space 39 can also be said to be divided, thanks to the pipe profile 20 arranged spirally, in which the heat-transfer medium 27 circulates along the channel arranged for it by the pipe profile 20. The channel winds throughout the entire length L of the tank structure 13 and thus also of the reactor space 14 inside it, acting on it in every direction. Here, the division of the hollow space 39 refers to its division to profile pipes parallel consecutively, according to the pitch defined by the spiralling pipe profile 20, in the reactor tank's 13 longitudinal direction L. In other words, in the reactor tank's 13 longitudinal direction L, the hollow space 39 is not unified, but winds around reactor space 14, rising in the reactor's 10 longitudinal direction L.

Figure 5:
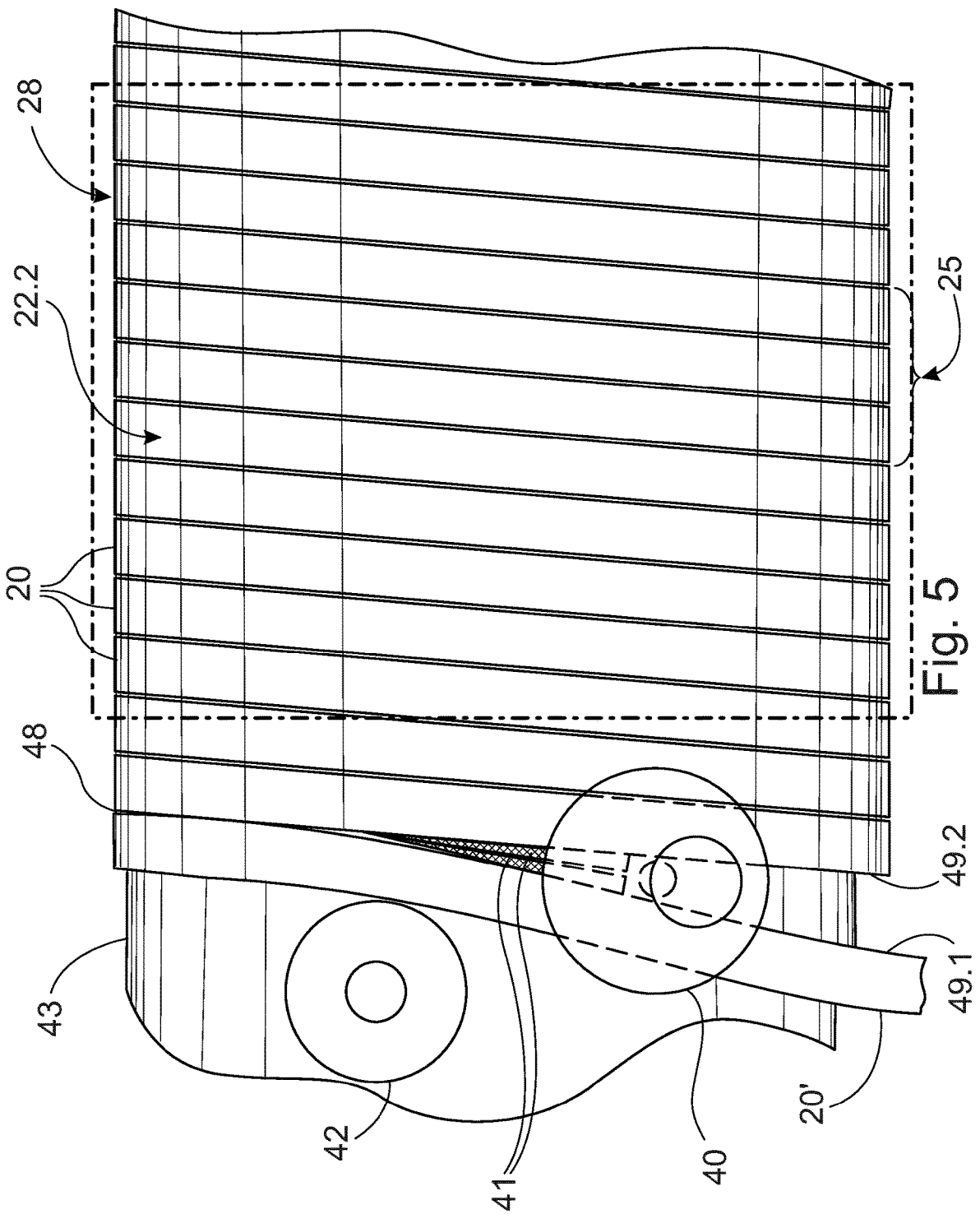
FIG. 5 shows an example of the tank structure's manufacturing principle.
Figure 6:
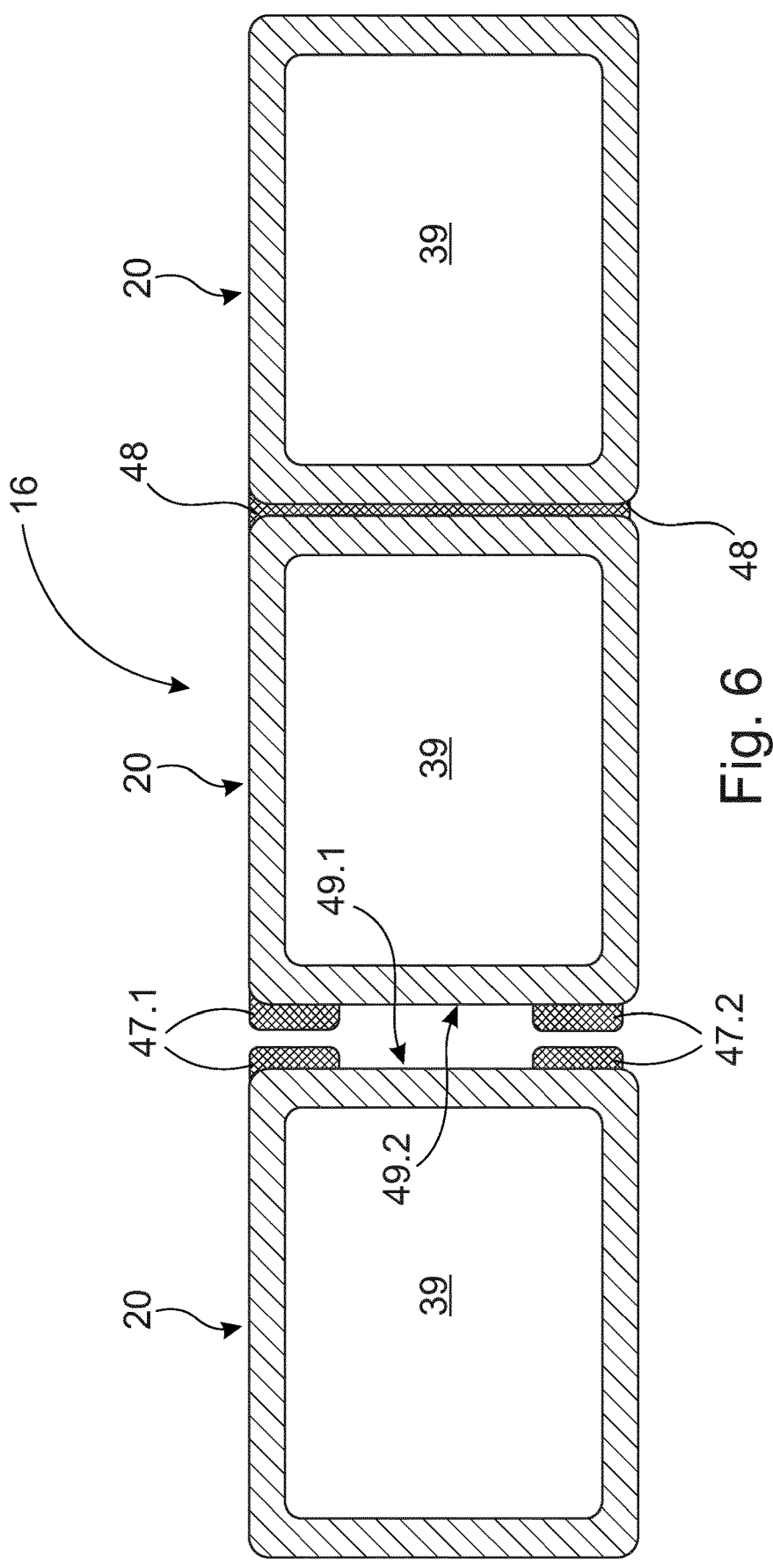
FIG. 6 shows an example of the joining together of the profile pipe forming the double-layer structure of the tank structure.

FIG. 5 shows the manufacture of the tube 28, i.e., the tank structure 13 and FIG. 6, for its part, the joining of the pipe profiles 20 to each other, as some possible embodiments. In it, during the helical winding, the hollow pipe profile 20' is joined on its side surfaces 49.1, 49.2 by a welding method to the already previously formed tubular structure 28. The joining takes place to the side surface 49.2 of the continuous pipe profile 20 joined in a corresponding manner to the tubular structure 28. As a result of the joining, a wall 35 of the tank structure 13 and heat-transfer-medium channel is formed for the biogas reactor 10 from the pipe profile 20. Thus, the tube 28 is formed from the pipe profile 20 by the welding method, in connection with its helical winding. According to one embodiment, the pipe profile 20' can be made immediately before, for example, its helical winding and joining to the tubular structure 28, for example, by extrusion or some other corresponding method. Ready pipe profile 20' can also be discharged from a reel to be wound helically to form the tubular structure 28. The result of the manufacturing process is a tubular continuous elongated and tight structural wall 35 in the form of a solid of revolution. In it the pipe profile 20 is helically wound and thus joined with a rise, i.e., spirally, to each other by their side walls 49.1, 49.2 thus forming a double-layer spiral structure for the tank structure's 13 wall 35. According to one embodiment, the tank structure 13 formed from pipe profile 20 will alone withstand the entire loading cause by the organic matter 11 on the biogas reactor 10. There will then be no need for a separate load-bearing frame to be arranged around the tank structure 13.

According to the example shown, the pipe profile 20' is wound, as shown in FIG. 5, helically onto a welding drum 43, at the same time as the profile surfaces 49.1, 49.2 to be welded together are heated to the desired temperature, for example, using hot air. After this, the welding mass 41 is, for example, extruded onto the heated profile surfaces 49.1, 49.2 in two strands 47.1, 47.2, for example, along each edge of the profile surface 49.1, 49.2, and the pipe-profile parts 20', 20 coated with welding mass are pressed together with the aid of at least one press roll 42. The press roll's 42 shaft can be aligned radially relative to the welding drum 43, so that a double welding joint 48 is formed between adjacent pipe-profile rounds. Welding is performed, for example, using a welding head 40, which can be between the two profile surfaces 49.1, 49.2 to be welded together. One skilled in the art will understand that this is only one example of a method to make the tube 28, which is now based on welding.

According to one embodiment, the hollow pipe profile 20 has, according to FIGS. 3, 4, and 6 a mainly rectangular cross-sectional shape. Having a rectangular shape, the pipe profiles 20 are easy to attach to each other by their side walls 49.1, 49.2. In addition, in its profile it is sufficiently rigid, and it also forms a flat inner surface to the side of the reactor space 14. In addition, openings can be easily made in the rectangularly shaped pipe profile 20 for various connections, which are, for example, connections 19.1-19.3 for removing biogas 12 from the reactor space 14 and/or connections 26.1-26.4 for leading heat-transfer medium 27 into and out of the hollow space 39 formed by the pipe profile 20 and progressing helically in the longitudinal direction L of the biogas reactor 10. Because microbes are sensitive to rapid changes in temperature, the plastic material's good insulation/poor heat transmission now create an even heat transfer to the organic matter 11 over a large surface area. The microbe strains then remain at the most even temperature and in the most favourable conditions as possible. This is essential for the operation of an unbroken process. Thus, the biogas reactor 10 according to the invention permits biogas 12 to be produced better also by using the thermophilic process thanks to good controllability and precise heating.

The pipe profile 20 can also be seen as a perforated profile. It is thus closed from the jacket. In other words, it is not divided longitudinally from the jacket, such as, for example, is the case with a half-pipe profile. The attachment of the pipe profiles 20 to each other then takes place from their side surfaces 49.1, 49.2.

The profile wall 25 on the outside 22.2 of the tube 28 formed from hollow pipe profile 20 includes connections 26.1-26.4 arranged to lead the heat-transfer medium 27 to the hollow pipe profile 20 and/or to remove it from the hollow pipe profile 20, more generally, from the wall 35 of the tank structure 13. Because the size of the biogas reactor 10 can be scaled in its longitudinal direction L, the number of heating connections 26.1-26.4 can vary accordingly. The heating connections 26.1-26.4 are arranged in the middle of the profile wall 25 on the outside 22.2 of the tube 28 formed from pipe profile 20.

According to a first embodiment, the gas connections 19.1-19.3 can be arranged, as shown in FIG. 3, between the pipe profiles 20. Thus, they are then in the area of two adjacent pipe profiles. In addition, they extend through the double wall 35 formed by the pipe profile 20 into the reactor space 14, to lead gas out of the reactor space 14. Being between the pipe profiles 20, the gas connections 19.1-19.3 do not prevent the circulation of the heat-transfer medium 27 in the hollow spaces 39 of the pipe profiles 20, i.e., in the spiral heat-transfer-medium channel formed by the pipe profile 20 on the tank structure's 13 jacket, as the gas connections 19.1-19.3 do not block the entire pipe profile 20.

Figure 9:
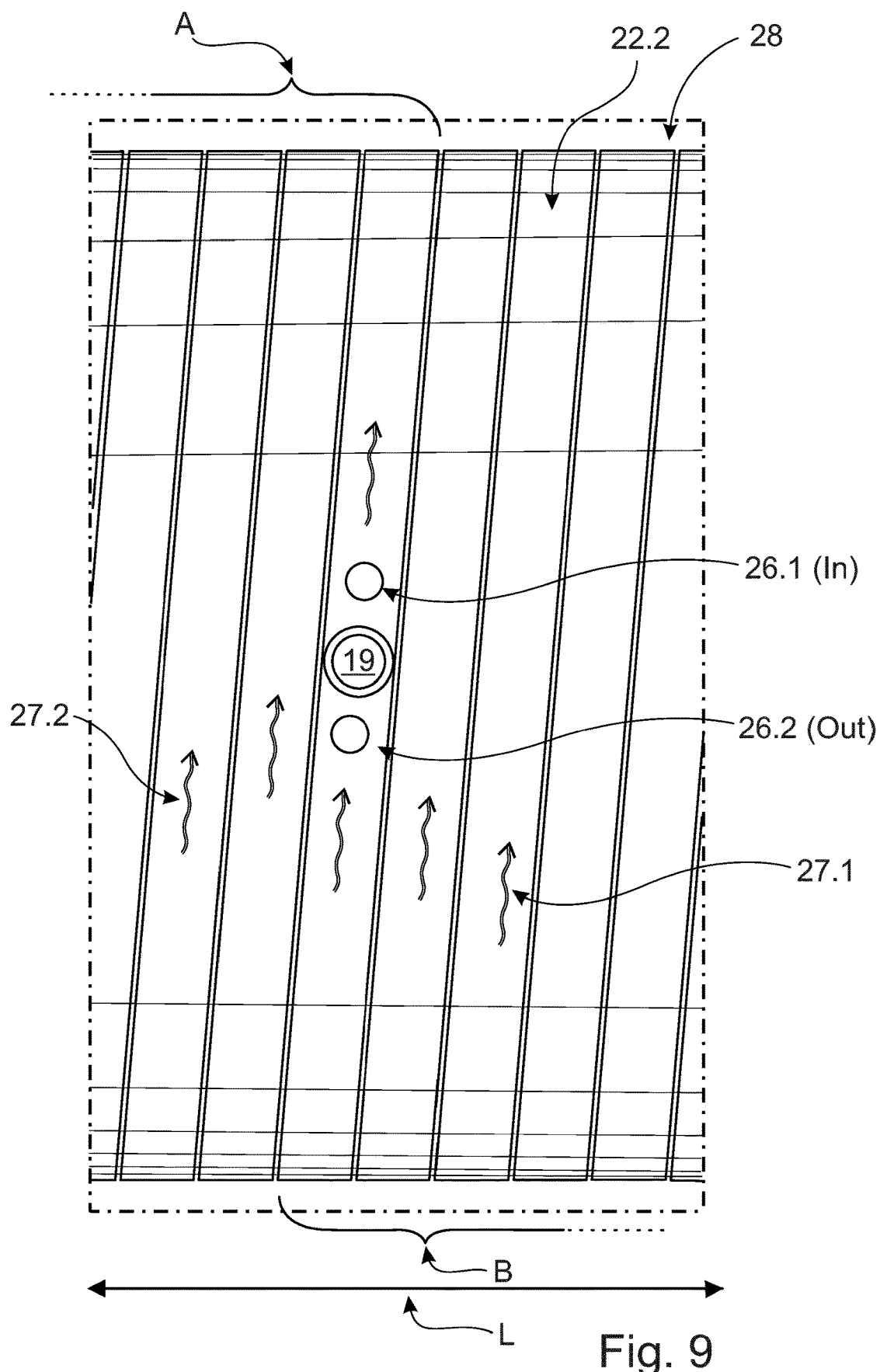
FIG. 9 shows schematically one way to arrange the gas and heat-transfer medium connections in the tank structure's wall.

According to yet another embodiment, the gas connection 19 can, if necessary, also be placed in the centre of the pipe profile 20 and the heating circulation connections 26.1, 26.2, for example, on both sides of the gas connection 19 in the pipe profile's 20 winding direction. FIG. 9 shows schematic example of this. The pipe profile 20, and thus also its heat-medium circulation to be arranged inside, are then intentionally blocked by the gas connection 19. For their part, the heat circulation connections 26.1, 26.2 are then arranged before the gas connection 19 and after the gas connection 19, in the direction of winding of the pipe profile 20.

The arrangement permits many different possibilities for leading the liquid acting as the heat-transfer medium 27. The heating zones A, B can be connected consecutively in series or partitioned to form their own circuit, such as, for example, FIG. 9 shows. When the gas connection 19 acts as a divider, in the reactor's 10 longitudinal direction L, of the hollow space 39 arranged helically, the heat-transfer medium 27 can be led, for example, in opposite directions in the reactor's 10 longitudinal direction L. Then both of the connections 26.1, 26.2 are feeds of the heat-transfer medium 27. On the other hand, the heat-transfer medium 27.1, 27.2 should then possibly be led, in the reactor's 10 longitudinal direction L, also in such a way that heating is performed in stages in the reactor's 10 longitudinal direction L, precisely as shown in FIG. 9. In other words, one heating zone A can then end at gas connection 19 in the reactor's 10 longitudinal direction L and the following, second heating zone B can start after gas connection 19. In this way, the biogas reactor's 10 heating can be controlled even more precisely and optimized the temperature correctly, for example, to suit each digestion stage. At one site, it can suffice for the heating liquid 27 to be led into the reactor 10 at one end and out at the other. At some other site, it can be necessary to regulate the optimal temperatures according to the various anaerobic decomposition stages (hydrolysis/acidogenesis/acetogenesis/methanogenesis), i.e., to divide the reactor 10 into as many as four different heating zones in its longitudinal direction L. More generally, according to the embodiment shown, one or more of the connections 19 for removing biogas 12 from the reactor space 14 are arranged to close the pipe profile 20 to divide the spiral hollow space 39 into heating zones A, B.

One commercially available example of a pipe product made from hollow pipe profile 20 is Uponor Ltd's pipe marketed under the trade name Weholite. Another commercially available example of a pipe product made from such a hollow pipe profile 20 is the pipe marketed under the trade name Kennorol by Parkanon Muovituote Ltd. Their use is known, for example, from water draining in earthworks.

An example of such a pipe-profile 20 material is a thermoplastic suitable for the purpose, such as, for example, polyethylene (PE) or polypropylene (PP). The pipe profile 20 of plastic material can also contain fibre reinforcement. It is very easily and rapidly machinable, which is a manufacturing-technical advantage. Yet another example of plastic can also be an antistatic plastic. A biogas-reactor 10 of plastic material, for example, PE plastic, will also withstand additives possibly used in biogas 12 production, if it is wished to improve production with additives. Some examples of these are lye, baking soda, or trace elements.

Thanks to the use of a tube 28 made using, for example, the method described above, it is possible to give the biogas reactor 10 good scalability. The size of the reactor 10 is easily scalable, for example, from a diameter of 0.5 m up to 6 metres. In addition to the diameter, the length of the reactor 10 can easily be changed, for example, according to the delay time of each customer's feed. Thus, owing to the invention it is possible to dimension and make reactor spaces 14 corresponding in their size (diameter/length) to each customer's requirements. There are several different pipe sizes commercially available that permit this.

The inner wall 23 of the tube 28 forming the tank structure 13 defining the reactor space 14 can be formed on the profile wall 22.1 of the pipe profile 20 on that side. The inner wall 23 itself is mainly smooth, though the spiral nature of the pipe profile 20 may nevertheless be more or less visible in the form of the welding seam 48. In FIG. 4, the seams are shown exaggeratedly slightly protruding, to illustrate them. The tube's 28 inner wall 23 does not necessarily require special coating, instead the material of the pipe profile 20 and thus the tubular structure 28 formed of it will withstand, for example, challenging process conditions and possible additives, being of, for example, PE plastic. This also helps to improve heat transfer, because extra intermediate layers between the hollow space 39 and the reactor space 14 are not needed.

On the other hand, the reactor space 14, i.e., the tubular structure's 28 inner wall 23 can, however, also be equipped with sheathing, for example, to improve its wear resistance. One possibility is to coat the inner wall 23 of the tube 28 forming the tank structure 13, at least part over the reactor space 14, for example, to improve its wear resistance, if foreign substances are mixed with the organic matter 11. The reactor space 14 then gains a smoother surface and also a greater material thickness. The coating 21 or more generally the sheathing can be on at least part of the tank structure's 13 inner wall 23. It can then be in the lower part of the reactor space 14 and can cover, for example, 20-70% of the inner wall's 23 circumference. One purpose of the coating 21 can be to prevent damage to the inner wall 23, as there can be, for example, foreign objects in the organic matter 11.

Sheathing can also be implemented, instead by coating, for example, by one or more wear plates. These can be arranged on the inner wall 23 of the tube 28 forming the tank structure 13 and arranged to define the tubular reactor space 14. The coating 21 or wear plate arranged to define the reactor space 14 is arranged against the profile wall 22.1 of the pipe profile 20, which is arranged to form the tube's 28 inner wall 23. The thickness of the coating 21 or more generally the sheathing 21' can be 1-20 mm, depending on its material. The coating 21 or more generally the sheathing 21' can also be of a plastic material. The coating 21 can also be used to increase the smoothness of reactor space's 14 walls. In other words, the profile pipes 20 in the direction of the reactor space 14 and the welding seams 48 between them are then not seen at all, at least to any substantial extent. The coating 21 or more generally sheathing 21' is, however, in no way essential, as the welding seam 48 between the profile pipes 20 is itself already very smooth, so that no substantial discontinuities, such as ridges or valleys, form on the tube's 28 inner wall 23.

The sheathing's 21' or coating's 21 thickness has, however, no effect on the profile pipe's 20 diameter and particularly on the stiffening and thus load-bearing nature of the tank structure 13. In other words, it has no essential effect in stiffening the overall structure and thus also no significance on the biogas reactor 10, for example, in terms of forming the self-supporting tank structure 13. Most of it is formed using a helically wound profile pipe 20, which in the biogas reactor 10 is also used as a means of temperature regulating of the reactor space 14 and thus of the organic matter 11 to be placed in it. The biogas reactor 10 is well insulated by insulation of the outside of the tank structure 13. The insulation is arranged, for example, directly on the surface of the tank structure 13, i.e., of the tube 28 it forms. The biogas reactor 10 can also be equipped with a base 37.

Figure 7:
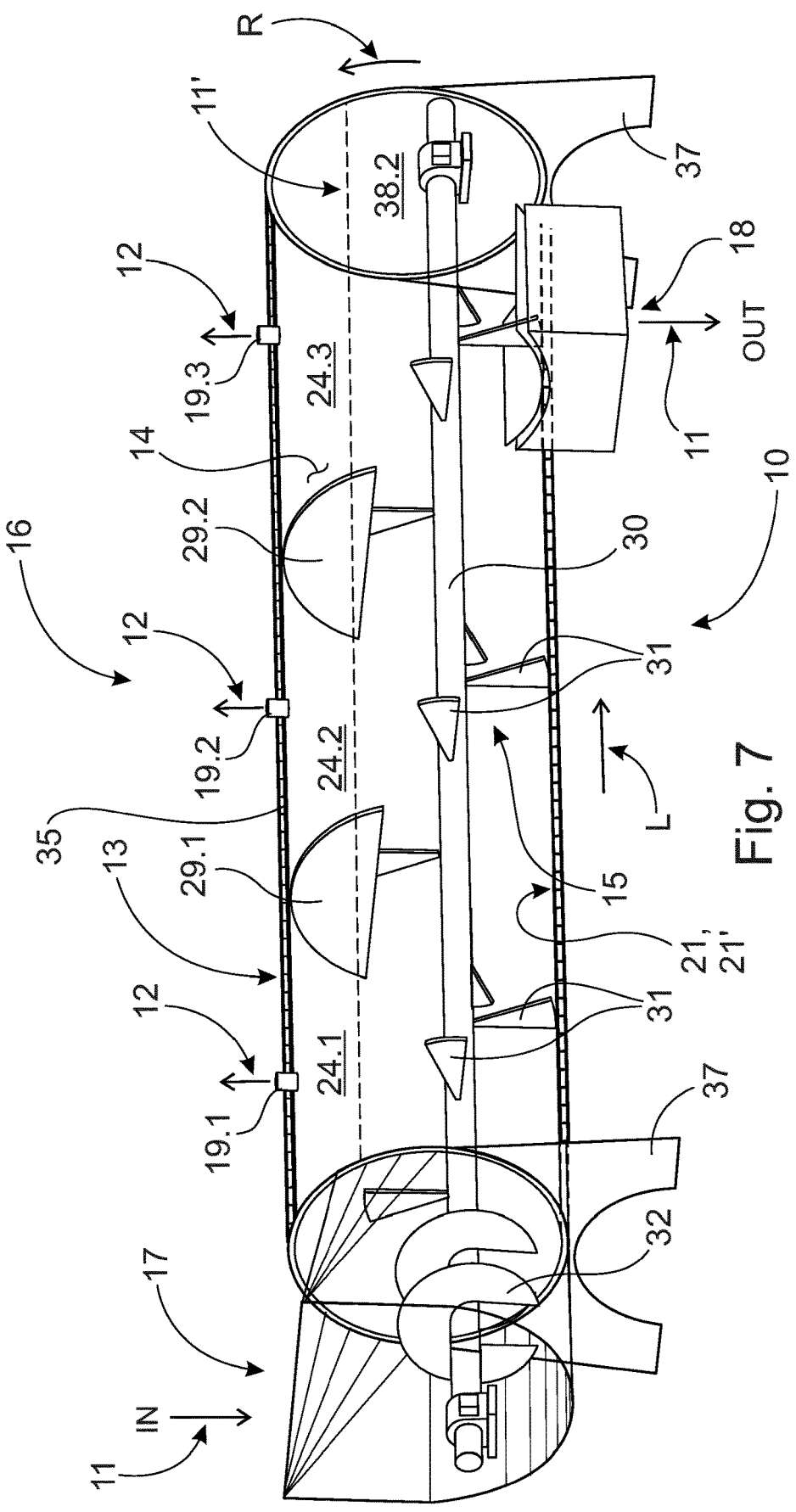
FIG. 7 shows a schematic example of the biogas reactor shown in FIGS. 1 and 2, with its reactor space now equipped with mixing.

FIG. 7 shows a schematic example of one biogas reactor 10 according to the invention, its reactor space 14 being now also equipped with mixing and, in addition, in this case now also with partitioning. The biogas reactor 10 then includes mixing means 15 arranged to act on the reactor space 14 to mix the organic matter 11 in the reactor space 14. The mixing means 15 include, in the embodiment shown in the figure, a rotation shaft 30 arranged in the reactor space 14 in the reactor space's 14 longitudinal direction L. Blades 31, wings, or similar mixing elements are arranged to the rotation shaft 30 in the radial R direction of the reactor space 14. The mixing means 15 are used to mix the organic matter 11 in the reactor space 14 in a set manner, for example, to maintain the gas-forming process. The mixing means 15 then, for example, disperse the organic matter 11 mechanically, so that it cannot form larger lumps, for example, on the bottom of the reactor space 14. In addition, the blades also submerge 2-layer material that may be floating on the surface of the organic matter 11. In other words, the mixing means 15 are also used to homogenize the matter 11. The biogas reactor 10 can also be implemented even without the mixing means 15. This is particularly the case in long reactors 10.

According to one embodiment, the mixing means 15 are arranged to also move the organic matter 11 placed in the reactor space 14 forwards in the reactor space's 14 longitudinal direction L. To implement this the blades 31 can be slightly twisted, like, for example, aircraft propellers. They then also act to create a flow in the organic matter 11 in the reactor space 14 and thus to push it towards the reactor's 14 outlet end 38.2, in which there can be an outlet opening. According to one embodiment, possible mixing can also be achieved by pumping with one or more pumps. During pumping the organic matter 11 can be, for example, circulated.

As can be seen, for example, from FIGS. 1, 2, and 7, the tubular reactor space 14 can also be partitioned into two or more gas chambers 24.1-24.3. For this purpose, the reactor space 14 can be, for example, partitioned by bulkheads to separate the chambers from each other. Gas bulkheads 29.1-29.3 creating partitioning are arranged in the upper parts of the reactor space 14, i.e., also of the chambers 24.1-24.3. They can be, for example, welded onto the inner wall 23. With the aid of the chambers 24.1-24.3 the gas-forming can be measured in the various stages of the process and the feed's through-put time optimized with the aid of the measured data. The aim is then to maximize the reactor's 10 loading and thus to reduce the reactor's physical size. By studying the speed of gas formation and the gas's 12 methane content as the process progresses, the feed, i.e., the through-put time of the organic matter 11, as well as the feed amounts of possible additives can be optimized.

It should be noted that the biogas reactor 10 can equally also be implemented without the partitioning described. In addition to or instead of partitioning, the bulkheads 29.1-29.3 can also be intended to reinforce the construction of the tank 13 itself. This is particularly the case in long reactors. On the other hand, the partitioning, for example, by bulkheads 29.1-29.$n$ of the gas 12 forming and removal as described in the present application can also be used to implement of the tank's 13 structural principle in other kinds of reactors. Thus, it can act as its own independent structural solution without being bound to any particular tank structure, such as, for example, the honeycomb structure wall 35 of the tank 13 according to the invention. Then too the partitioning allows the speed and gas content of the gas formation to be studied. The partitioning described in connection with the tank structure 13 according to the invention, for example, using bulkheads 29.1-29.3 however achieves an advantage in the sense that the reactor space's 14 temperature can be regulated, thanks to the tank structure according to the invention, by chamber 24.1-24.$n$ and in that way the biogas formation can be performed in the same one reactor structure as single process stage precisely controlled by partition. In other words, the partitioning combined with the tank structure 13 formed by helical winding to adapt it to operate to maintain the reactor space's 14 temperature in a controlled manner, together achieve a particular advantage in terms of the control of the gas formation. Owing to the invention, the temperatures can vary in different partitions and a structure to achieve their regulation can be easily implemented by a helically wound spiral pipe structure.

The solids content of the organic matter 11 to be processed in the biogas reactor 10 can be, for example, such that it is in a fluid form. One can then also speak of a viscous fluid sludge, or a fluid viscous mass. The organic matter 11 is pre-processed to be as fine as possible. Its particle size can be, for example, a maximum of 5 cm. An example of the solids content of the organic matter 11 is less than 35%. There is then not necessarily any need to equip the biogas reactor 10 with means to move the organic matter 11 forwards in the reactor space 14, instead its movements, and exit from the reactor space 14 takes place by itself These mixing means' 15 function can thus also be purely mixing without a special transfer function. The pump can operate for either or both of those purposes.

According to one embodiment, the bulkheads referred to above can be arranged to the upper part of the reactor space 14 in such a way that the chambers 24.1-24.3 are arranged to be separated from each other by the bulkheads 29.1-29.3. In addition to the bulkheads 29.1-29.3, the organic matter 11 to be placed in the reactor space 14 can also be used to separate the chambers 24.1-24.3 from each other. The organic matter 11 is then arranged to be sealed to the lower parts of the bulkheads 29.1-29.3. For this purpose, the organic matter's 11 surfaces height, i.e., surface 11' in the reactor space 14 can be arranged in such a way that the organic matter 11 seals against the surfaces formed by the bulkheads 29.1-29.3. Thanks to this the chambers 24.1-24.3 arranged for the biogas 12 are separated from each other on the water-trap principle. Thus, the chambers' 24.1-24.3 gas seal takes place by the organic matter 11 exceeding the lower edge of the bulkheads 29.1-29.3, which thus creates the relevant gas seal. To measure the surface height, there is sensing in the reactor space 14, for which there is at least one connection 33 in the tank structure 13.

According to one embodiment, blades 31 belonging to the mixing means 15 are arranged to the rotation shaft 30 at least at the locations of the bulkheads 29.1-29.3 creating the partitioning of the reaction chamber 14. In addition to mixing the matter 11, their purpose is also then to keep the bulkheads' 29.1-29.3 surfaces clean using the wiper principle. The blades 31 sweep over the bulkheads 29.1-29.3 and thus clean them mechanically by wiping. The length of the shaft 30 and/or the blades 31 can in turn be arranged so that the blades 31 also extend to the reactor space's 14 bottom or at least close to it.

According to one embodiment, the biogas reactor's 10 feed, mixing, and layering-prevention can be done even using the same shaft 30. At the start of the shaft 30, i.e. at the biogas reactor's 10 feed end, there can then be a feed screw 32, as shown in FIG. 7. It is used to move the organic matter 11 into the reactor space 14. By such a structural solution, the biogas reactor's 10 internal-load energy can be minimized, for example. In addition, fault sensitivity is reduced, and improved operating reliability is achieved.

In the tank structure 13 there can be in addition one or more connections 36.1-36.4 for circulating the organic matter 11 (FIG. 2). One purpose of circulation can be to stabilize the process. Sampling and possible additive dosing can also be carried out from these connections 36.1-36.4.

Figure 8:
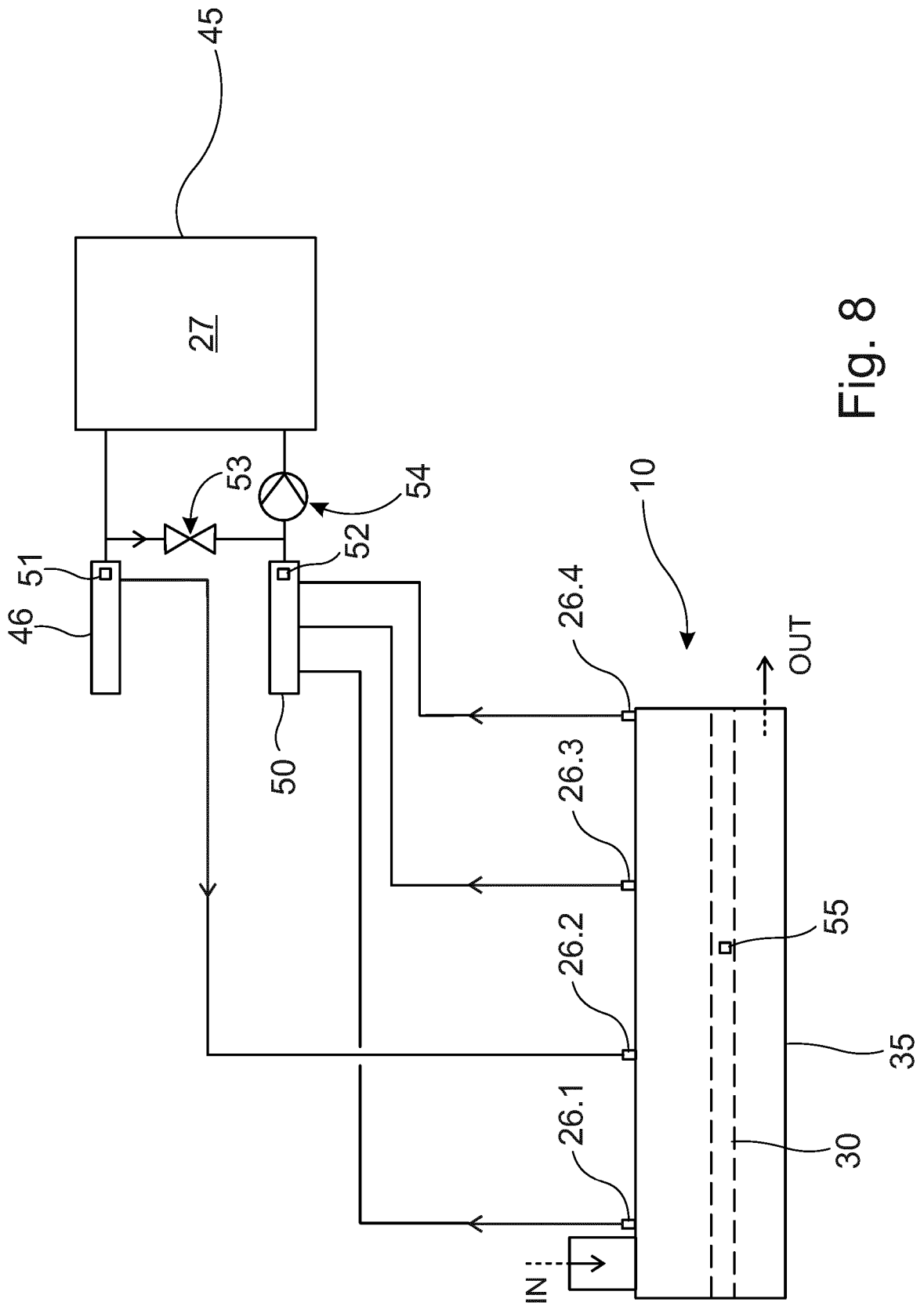
FIG. 8 shows a rough schematic diagram of an example of the biogas reactor's heat-control circuit.

FIG. 8 shows a rough schematic diagram of one example of the biogas reactor's 10 heat-control circuit. Outside the biogas reactor 10 there can be, for example, an electrical (gas) boiler 45, which is connected to the connections 26.1-26.4 by means of the pipelines connected to the heating tube 46. FIG. 8 also shows the flow directions of the liquids. The circuit is formed in such a way that it is arranged to guide a large amount of heating energy to the biogas reactor's 10 starting end, i.e., to the feed-adding end (IN). Regulation takes place in turn by altering the heat-transfer medium's 27 circulation velocity. The end part of the reactor 10 is sought to be kept at as even a temperature as possible.

According to another embodiment, the heat-transfer circuit can also be, for example, like that shown in FIG. 1, in the case of its inlet/outlet connections. The inlet is from connections 26.2 and 26.4 and the outlet, in turn, from connections 26.1 and 26.3. Then, for example, the heat-transfer liquid 27 led in from the connection 26.2 divides to the reactor's 10 inlet and outlet sides and the liquid outlet through connection 26.3 is from both directions in the reactor's 10 longitudinal direction L. By plugging the gap between two adjacent connections, for example, by the gas removal connection 19, the heat-transfer-medium's 27 inlet/outlet connections can be arranged nearly next to each other, as shown in FIG. 9.

In the embodiment shown in FIG. 8, regulation can be, for example, as follows. All the heating liquid is led in from connection 26.2. 50% of the heating liquid is led out from connection 26.1 and 25% of the heating liquid is led out from each of connections 26.3 and 26.4. The division can be created, for example, through the size of connections 26.1, 26.3, 26.4. In the same time, more liquid can be released from the larger connection 26.1 on the inlet side of the reactor space 14 relative to the inlet connection 26.2, than is released from the smaller connections 26.3, 26.4 on the outlet side of the reactor space 14 relative to the inlet connection 26.2. In other words, the liquid then remains longer in the reactor's 10 latter half relative to inlet connection 26.1.

To state the aforesaid regulation example even more generally, at least one connection 26.2 of the connections is the heat-transfer medium's 27 inlet feed, which is arranged to lead the heat-transfer medium 27 into the hollow pipe profile 20. In this case, the feed takes place to the biogas reactor's 10 central area. One or more of the connections 26.1, 26.3, 26.4 are, in turn, outlets arranged to remove the heat-transfer medium 27 from the hollow pipe profile 20 before and/or after at least one inlet feed. In addition, at least one connection 26.1 of the outlet feeds is arranged before the inlet feed and one or more of connections 26.3, 26.4 are arranged after the inlet feed. Further, at least one of the outlet connections 26.1, being now before the inlet feed, is arranged to be removed more heat-transfer medium 27 than the individual connections 26.3, 26.4 after the inlet feed.

Temperature sensing of the biogas reactor 10 can be implemented, for example, as follows. Temperature sensors 51, 52, arranged to measure temperature, are arranged in the heating circulation on its inlet side in a heating manifold 46 and separately on its return side in a collector manifold 50. There can then be a common temperature measurement for all the inlet connections 26.2 and correspondingly a common measurement for the return side in the header tube 50. Inside the mixing shaft 30 too there can also be its own temperature measurement 55, at least at one point. When scaling the reactor 10 to be longer in the longitudinal direction L, there can also be several temperature-measurement points inside the shaft 30. The circulation velocity of the heating liquid 27 is suitable if the return heat and the temperature measured inside the shaft 30 are as close as possible to each other. Thus, the temperatures are compared. The circulation is kept large enough that the inlet temperature is only slightly greater, at a maximum of, for example, 4° C. This is influenced by the reactor's size class. In the circuit of FIG. 8, a mixing valve 53 and a heating-liquid 27 circulation pump 54 are also shown as circuit accessories.

In addition to a biogas reactor 10, the invention also concerns a method for producing biogas 12. In the method, biogas 12 is produced from organic matter 11 using a biogas reactor 10 in a temperature-regulated manner. The biogas reactor 10 is the biogas reactor described above.

Further, the invention also concerns a method for manufacturing a biogas reactor 10. The biogas reactor 10 is intended to produce biogas 12 in a temperature-regulated manner from organic matter 11 in a tubular reactor space 14 formed by a tank 13. The biogas reactor's 10 tank 13 is formed by a tube 28 made by a welding method, in which hollow pipe profile 20 is arranged by helical winding in a spiral arrangement to form a wall 35 for the tube 28 being made. In this context, the term welding method refers to the pipe profiles 20 being joined together by their side walls 49.1, 49.2, for example, by heating, or some other possible manner of attachment. The side walls 49.1, 49.2 of the pipe profiles 20, or the material arranged between them, then melt, the pipe profiles 20 then attach to each other by their side walls 49.1, 49.2 and when cooled are joined to each other. Thus, welding can also be understood as the gluing of the pipe profiles 20 to each other by their side walls 49.1, 49.2, for example, with the aid of heat. In addition, in the method the tube 28 is equipped with connections for forming biogas 12, which are at least one gas connection 19 and one or more connections 26.1-26.4 for a heat-transfer medium 27.

Really long reactor structures can be delivered to the operating site, for example, in parts and joined together, for example, by hot welding or by screw connections arranged to the ends of the tubes 28. The handing of the helical nature of the pipe profile 20 can then even vary between different parts forming the tank structure 13. Flange connection is also one alternative for joining parts to each other.

A reactor tank 13 formed of plastic material is economical also in terms of arranging the connections 19.1-19.3, 26.1-26.4. Holes can be drilled in the reactor tank 13 at the desired location for a connection, to which the connection is then screwed, for example, on the machine-screw principle, i.e., without a separate thread. Thus, connections particularly for the heat-transfer-medium circulation can be added as required even as a retrofit on site, without the reactor 10 needing to be separately moved anywhere, or special means being needed to arrange the connection.

The invention also concerns the use of a tube 28 made from a hollow pipe profile 20 by a welding method and by helical winding into a spiral arrangement as a temperature-regulated biogas reactor 10, and even more particularly as the tank structure 13 of a biogas reactor 10.

One example of the tank structure's 13 dimensions is a diameter of 1 m and a length of 5 m. One example of the pipe profile 20 has dimensions of 70 mm×40 mm. The pipe profile's 20 wall thickness can be, for example, 4-8 mm.

In addition to implementing heating means 16, the biogas reactor 10 according to the invention's structural implementation is light. In addition, the biogas reactor 10 according to the invention has good scalability. The biogas reactor 10 according to the invention can, within the restrictions of volume capacity of transport means, be transported to its operating site even as only a single component, thus avoiding, for example, its assembly at the operating site. This reduces the costs relating to the making and acquisition of the biogas reactor 10 and thus also shortens the pay-back time of the investment.

The invention's objects have been described above largely with reference to biogas. There is, however, reason to note that, in the context of the invention biogas can be understood in an appropriate context. More generally, as also stated, it is gas formation from material containing organic matter. Most conventionally it is known as the formation of a methane-rich gas, but equally it can also be, for example, the formation of hydrogen from material containing organic matter, either as its own process or then, for example, combined with methane production. According to one exemplary embodiment, the organic matter can then be, for example, turf. Crushed turf can be pre-treated, for example, with lye before being processed in the reactor structure according to the invention. According to the embodiment, the process taking place in the reactor can then in its initial stage produce hydrogen-rich gas, which can then be followed by methane production. On the other hand, the reactor 10 according to the invention can equally be used only for hydrogen production from material containing organic matter.

It should be understood that the above description and the related figures are intended only to illustrate the present invention. The invention is thus not restricted to only the embodiments described above or defined in the Claims, instead many different variations and adaptations of the invention, which are possible within the scope of the inventive idea defined by the accompanying Claims, will be obvious to one skilled in the art.

The invention claimed is:

1. A biogas reactor comprising:
   a tank structure comprising a hollow pipe profile helically wound in a single spiral arrangement, the hollow pipe profile having outer side surfaces joined together by thermoplastic joining to form the tank structure, and wherein the hollow pipe profile itself forms a tank wall having a double-layer structure enclosing a tubular reactor space arranged inside the tank structure in which an organic matter can be placed to form biogas, wherein a spiral hollow space exists within the double-layer structure of the tank wall itself to accommodate a heat-transfer medium to influence a temperature of the organic matter placed in the tubular reactor space;
   connections to feed the organic matter to the tubular reactor space and to remove the organic matter from the tubular reactor space; and
   at least one connection to remove biogas from the tubular reactor space.

2. The biogas reactor according to claim 1, wherein a cross-section of the hollow pipe profile has mainly a rectangular shape.

3. The biogas reactor according to claim 1, wherein the tank structure includes an inner wall having a surface facing the tubular reactor space that is one of at least partially coated and at least partially sheathed to increase wear and/or smoothness of the inner wall surface.

4. The biogas reactor according to claim 3, wherein the inner wall comprises a profile wall of the hollow pipe profile wound to form the tank structure.

5. The biogas reactor according to claim 1, further including bulkheads spaced apart along a length of the tubular reactor space and attached to an upper inner surface of the tank structure forming the tubular reactor space, so that when a surface height of organic matter in the tubular reactor space is sufficient to seal against a lower extremity of the bulkheads, two or more chambers are formed separated from each other by the bulkheads.

6. The biogas reactor according to claim 1, wherein an outer layer of the double-layer structure of the hollow pipe profile forming the tank structure comprises at least one connection arranged to at least one of lead the heat-transfer medium into the hollow pipe profile and to remove the heat-transfer medium from the hollow pipe profile.

7. The biogas reactor according to claim 6, wherein:

at least one of the connections comprises an inlet feed arranged to lead the heat-transfer medium into the hollow pipe profile; and at least one of the connections comprises outlets arranged to at least one of remove the heat-transfer medium from the hollow pipe profile before and after the at least one inlet feed.

8. The biogas reactor according to claim 7, wherein:

at least one connection of the outlets is arranged before the inlet feed; and at least one connection of the outlets is arranged after the inlet feed.

9. The biogas reactor according to claim 8, wherein at least one connection of the outlets before the inlet feed is arranged to remove more heat-transfer medium than individual connections after the inlet feed.

10. The biogas reactor according to claim 1, further comprising a mixer coupled to the tubular reactor space, the mixer comprising:

a rotation shaft arranged in a longitudinal direction of the tubular reactor space; and blades attached to the rotation shaft and extending in a radial direction of the tubular reactor space.

11. The biogas reactor according to claim 10, wherein the rotation shaft together with the blades are, in addition to mixing, arranged to move the organic matter placed in the tubular reactor space forwards in the longitudinal direction of the tubular reactor space.

12. The biogas reactor according to claim 10, further including bulkheads spaced apart along a length of the tubular reactor space and attached to an upper inner surface of the tubular structure forming the tubular reactor space, so that when a surface height of organic matter in the tubular reactor space is sufficient to seal against a lower extremity of the bulkheads, two or more chambers are formed separated from each other by the bulkheads, and wherein the blades are attached to the rotation shaft at least at locations of the bulkheads, and are arranged to create a partitioning of the tubular reactor space and to keep the bulkheads clean by wiping the bulkheads.

13. The biogas reactor according to claim 1, wherein at least one of the connections to remove biogas from the tubular reactor space is arranged to close the hollow pipe profile to divide the spiral hollow space into heating zones.

14. The biogas reactor according to claim 1, wherein the tank structure comprises a plastic material.

15. A method for producing biogas from organic matter in a temperature-regulated manner utilizing the biogas reactor according to claim 1.

16. The method according to claim 15 for producing biogas, comprising producing the biogas utilizing at least a thermophilic process.

17. A method of producing a temperature-regulated reactor according to claim 1, comprising utilizing a helically wound hollow pipe profile having outer side surfaces joined together by thermoplastic joining to form a single spiral arrangement enclosing a tubular reactor space for organic matter.

18. A biogas reactor comprising:

a tank structure comprising a hollow pipe profile helically wound in a spiral arrangement to form a wall having a double-layer structure enclosing a tubular reactor space arranged inside the tank structure in which an organic matter can be placed to form biogas, wherein a spiral hollow space exists within the double-layer structure of the wall to accommodate a heat-transfer medium to influence a temperature of the organic matter placed in the tubular reactor space, wherein the tank structure includes an inner wall having a surface facing the tubular reactor space that is one of at least partially coated and at least partially sheathed to increase wear and/or smoothness of the inner wall surface;

connections to feed the organic matter to the tubular reactor space and to remove the organic matter from the tubular reactor space; and at least one connection to remove biogas from the tubular reactor space.

19. A biogas reactor comprising:

a tank structure comprising a hollow pipe profile helically wound in a spiral arrangement to form a wall having a double-layer structure enclosing a tubular reactor space arranged inside the tank structure in which an organic matter can be placed to form biogas, wherein a spiral hollow space exists within the double-layer structure of the wall to accommodate a heat-transfer medium to influence a temperature of the organic matter placed in the tubular reactor space;

connections to feed the organic matter to the tubular reactor space and to remove the organic matter from the tubular reactor space;

at least one connection to remove biogas from the tubular reactor space; and bulkheads spaced apart along a length of the tubular reactor space and attached to an upper inner surface of the tank structure forming the tubular reactor space, so that when a surface height of organic matter in the tubular reactor space is sufficient to seal against a lower extremity of the bulkheads, two or more chambers are formed separated from each other by the bulkheads.

20. A biogas reactor comprising:

a tank structure comprising a hollow pipe profile helically wound in a spiral arrangement to form a wall having a double-layer structure enclosing a tubular reactor space arranged inside the tank structure in which an organic matter can be placed to form biogas, wherein a spiral hollow space exists within the double-layer structure of the wall to accommodate a heat-transfer medium to influence a temperature of the organic matter placed in the tubular reactor space;

connections to feed the organic matter to the tubular reactor space and to remove the organic matter from the tubular reactor space;

at least one connection to remove biogas from the tubular reactor space;

a mixer coupled to the tubular reactor space and comprising a rotation shaft arranged in a longitudinal direction of the tubular reactor space; and blades attached to the rotation shaft and extending in a radial direction of the tubular reactor space; and bulkheads spaced apart along a length of the tubular reactor space and attached to an upper inner surface of the tubular structure forming the tubular reactor space, so that when a surface height of organic matter in the tubular reactor space is sufficient to seal against a lower extremity of the bulkheads, two or more chambers are formed separated from each other by the bulkheads, and wherein the blades are attached to the rotation shaft at least at locations of the bulkheads and are arranged to create a partitioning of the tubular reactor space and to keep the bulkheads clean by wiping the bulkheads.

* * * * *